United States Patent [19]

Takahashi et al.

[11] 4,290,946
[45] Sep. 22, 1981

[54] PREPARATION OF HEXAMETHYLENEIMINE

[75] Inventors: Yasunobu Takahashi, Tokyo; Einosuke Fujimoto, Nobeoka; Toshio Shimizu, Nobeoka; Takeo Kato, Nobeoka, all of Japan

[73] Assignee: Asahi Kasei Kogyo Kabushiki Kaisha, Osaka, Japan

[21] Appl. No.: 598,914

[22] Filed: Jul. 24, 1975

[30] Foreign Application Priority Data

| | | |
|---|---|---|
| Jul. 25, 1974 [JP] | Japan | 49-84665 |
| Aug. 15, 1974 [JP] | Japan | 49-92756 |
| Oct. 8, 1974 [JP] | Japan | 49-115181 |
| Nov. 28, 1974 [JP] | Japan | 49-135875 |
| Mar. 13, 1975 [JP] | Japan | 50-29461 |

[51] Int. Cl.³ .................................................. C07D 295/02
[52] U.S. Cl. ................................................... 260/239 B
[58] Field of Search ...................................... 260/239 B

[56] References Cited

U.S. PATENT DOCUMENTS

| | | | |
|---|---|---|---|
| 2,232,059 | 2/1941 | Farlow | 260/239 B |
| 3,652,545 | 3/1972 | Horlenko | 260/239 B |
| 3,830,800 | 8/1974 | Brake | 260/239 B |
| 4,229,346 | 10/1980 | Toussaint . | |

FOREIGN PATENT DOCUMENTS

| | | | |
|---|---|---|---|
| 920606 | 2/1973 | Canada | 260/239 B |
| 2414930 | 10/1975 | Fed. Rep. of Germany | 260/239 B |

OTHER PUBLICATIONS

Yasumura, Chem. Abs. 59, 2813c (1963).

*Primary Examiner*—Mark L. Berch
*Attorney, Agent, or Firm*—Sughrue, Mion, Zinn, Macpeak and Seas

[57] ABSTRACT

A process for preparing hexamethyleneimine from hexamethylenediamine, which comprises continuously reacting hexamethylenediamine at about 70 to 180° C. in an inert solvent using a nickel catalyst and/or cobalt catalyst while maintaining the concentrations of hexamethyleneimine and hexamethylenediamine in the reaction mixture at 10% by weight or less and 25% by weight or less, respectively, by removing the hexamethyleneimine from the reaction system as soon as the hexamethyleneimine is formed.

12 Claims, No Drawings

PREPARATION OF HEXAMETHYLENEIMINE

BACKGROUND OF THE INVENTION

1. Field of the Invention

This invention relates to a process for preparing hexamethyleneimine from hexamethylenediamine at low temperatures and pressures, and more specifically, to a process for preparing hexamethyleneimine from hexamethylenediamine which comprises catalytically deaminating hexamethylenediamine in an inert solvent, and continuing the reaction while removing the resulting hexamethyleneimine immediately from the reaction system.

2. Description of the Prior Art

Hexamethyleneimine is an important compound which is useful as an intermediate material for pharmaceuticals and agricultural chemicals, and also finds a wide range of applications as rubber vulcanization accelerators and other rubber chemicals, ingredients for textile lubricants, antistatic agents and finishing agents, corrosion inhibitors for metals, and modifiers or cross-linking agents for resins.

Heretofore, hexamethyleneimine has been obtained in small quantities from by-products which occur in the production of hexamethylenediamine by catalytic hydrogenation of adiponitrile or in the production of hexamethylenediamine by catalytic ammonolysis of 1,6-hexanediol. It has also been reported in *Journal of the Chemical Society of Japan*, Vol. 82, page 1701 (1961) that hexamethyleneimine was obtained in a yield of about 10% by heating hexamethylenediamine together with Raney nickel at 160° to 170° C., but a greater part of the product consisted of a resinous product or tar.

*Chemische Berichte*, Vol 96, page 924 (1963) also discloses that by heating hexamethylenediamine together with Raney nickel at 142°–143° C. in a solvent such as benzene, xylene or mesitylene, hexamethyleneimine is obtained in a yield of 24 to 38% (as the picrate salt), but at the same time, 1,6-bis-hexamethyleneiminohexane is formed in a yield of 12 to 47% (as the picrate salt). Furthermore, Canadian Pat. No. 920,606 (1973) discloses that hexamethyleneimine is obtained in a selectivity of 47 to 87% by contacting hexamethylenediamine with a hydrogenation catalyst at 150° to 250° C. in the presence of hydrogen. However, since the conversion of hexamethylenediamine is as low as 17 to 44%, a large quantity of unreacted hexamethylenediamine must be recovered by distillation. It is also necessary to reduce the amounts of by-products by adding hydrogen and ammonia during the reaction.

SUMMARY OF THE INVENTION

The present invention relates to a process in which a high conversion of hexamethylenediamine and a high yield of hexamethylenediamine is maintained in the deamination reaction of hexamethylenediamine by inhibiting the formation of bis-hexamethylenetetramine, 6-hexamethyleneimino-1-aminohexane, 1,6-bis-(hexamethyleneimino)hexane, and polymeric amino compounds or a tar as by-products.

According to this invention, a process for preparing hexamethyleneimine is provided comprising continuously deaminating hexamethylenediamine using a nickel catalyst and/or a cobalt catalyst in an inert solvent while adjusting the concentration of hexamethylenediamine in the reaction mixture to about 25% by weight or less, and maintaining the concentration of the hexamethyleneimine in the reaction mixture at about 10% by weight or less by removing the resulting hexamethyleneimine immediately from the reaction system.

DETAILED DESCRIPTION OF THE INVENTION

The catalyst used in this invention is a nickel or cobalt type catalyst, examples of which include Raney nickel, Raney cobalt, reduced nickel, reduced cobalt, Urushibara nickel [i.e., as disclosed in *Bulletin of the Chemical Society of Japan*, Vol. 27, page 480 (1954); *Bulletin of the Chemical Society of Japan*, Vol. 33, page 232 (1960); *Chemical Abstracts*, Vol. 55, page 7332 (1961)], Urushibara cobalt, etc., These catalysts can be prepared by various methods under various conditions. Catalysts composed of these nickel and/or cobalt catalysts on carriers can also be used. Suitable carriers are, for example, alumina, $\gamma$-alumina, and kieselgur. The catalyst is usually employed in an amount of about 1 to 10% by weight to the weight of the hexamethylenediamine starting material.

As a result of attempts to develop a method for preventing the deactivation of such catalysts and a method for regenerating the deactivated catalysts, it has been found that when 1 to 5 parts by weight of sodium hydroxide is added to 100 parts of a Raney nickel catalysts, for example, the activity of the catalyst can be maintained for a period, e.g., about ten times longer than that in the case of using the Raney nickel catalyst alone. It has also been found that treatment of the catalyst, after preparation or re-use, with an ether is effective for maintaining the activity of the catalyst. In this treatment, tetrahydrofuran, dioxane, diethyl ether and dibutyl ether can, for example, be used as the ether, and it is especially effective to perform the treatment at an elevated temperature, e.g., about 50° C. or higher. To effect this treatment the catalyst is contacted with an ether in an amount effective to wash the catalyst.

One of the characteristic features of this invention is that the reaction is carried out in the presence of an inert solvent. The "inert" solvent is preferably one which does not react or reacts only with difficulty with the starting material, intermediates, reaction product and catalyst during the reaction, which permits the intended reaction to be performed smoothly and which can also be separated from the hexamethyleneimine. Suitable solvents which can be used include the following groups of solvents.

(1) Water;

(2) Aliphatic alcohols, alicyclic alcohols, and benzene ring-substituting aliphatic alcohols, such as ethyl alcohol, iso-propyl alcohol, n-propyl alcohol, n-butyl alcohol, 3-methoxybutyl alcohol, n-amyl alcohol, iso-butyl alcohol, n-hexanol, n-octanol, 2-ethylhexanol, dodecyl alcohol, cyclopentanol, cyclohexanol, methylcyclohexanol, methylcyclopentanol, $\alpha$-hydroxymethylcyclohexane, $\beta$-hydroxyethylcyclohexane, benzyl alcohol, $\beta$-hydroxyethylbenzene, tetrahydrofurfuryl alcohol, ethylene glycol, 1,4-butanediol, and 1,6-hexanediol.

(3) Aliphatic hydrocarbons, alicyclic hydrocarbons and aromatic hydrocarbons, such as n-hexane, n-heptane, n-octane, petroleum benzin, ligroin, methylcyclopentane, ethylcyclopentane, cyclohexane, methylcyclohexane, ethylcyclohexane, iso-propylcyclohexane, cyclooctane, cyclododecane, benzene, toluene, ethyltoluene, xylene, cumene, pseudocumene, durene, ethylbenzene, chlorobenzene, tetralin, and decalin.

(4) Aliphatic ethers having a boiling point of at least about 60° C. and aralkyl ethers, such as di-n-butyl ether, diisobutyl ether, ethyl butyl ether, di-n-amyl ether, dioxane, tetrahydrofuran, anisole, ethyl anisole, and phenyl propyl ether.

(5) Tertiary amines such as triethylamine, tributylamine, and N,N-dimethylaniline.

In order not to impede the reaction in accordance with this invention, any materials which would impede the reaction are removed sufficiently from these organic solvents prior to use.

Another feature of the present invention resides in reaction temperatures. The reaction temperature that can be used in this invention is about 70° to 180° C., preferably 80° to 150° C., most preferably 95° to 150° C. These reaction temperatures are lower than the reaction temperatures of 150° to 250° C. described in the prior art. Accordingly, the activity of the catalyst is maintained high for long periods of time.

A last and very important characteristic feature of this invention is that the concentration of the hexamethyleneimine in the reaction mixture is maintained low by effectively removing the resulting hexamethyleneimine produced from the reaction system as rapidly as possible during the reaction. A preferred concentration of the hexamethyleneimine is about 10% by weight or less, and it is more preferably 5% by weight or less, and most preferably 2% by weight or less. As a result, the formation of 6-hexamethyleneimino-1-aminohexane, 1,6-bis-(hexamethyleneimino)hexane, and polymeric amino compounds or tar, which are by-products from the hexamethyleneimine, can be inhibited, and the yield of hexamethyleneimine can be improved. For the same reason and in order to inhibit the formation of bis-hexamethylenetriamine, an intermolecular deamination reaction product of hexamethylenediamine, the concentration of the hexamethylenediamine in the reaction mixture is limited to about 25% by weight or less, preferably 10% by weight or less, by increasing the conversion of hexamethylenediamine or controlling the supply of the hexamethylenediamine.

The removal of the resulting hexamethyleneimine from the reaction system can be effected, for example, by the following methods.

(1) A method comprising distilling hexamethyleneimine effectively as an azeotrope using a solvent which forms an azeotrope with hexamethyleneimine, such as water.

(2) A method comprising using a solvent having a boiling point higher than that of hexamethyleneimine (more than 138° C.) and distilling the hexamethyleneimine together with a part of the solvent. When this method is used, the reaction is performed at atmospheric pressure or reduced pressure, e.g., about 400 to 30 mmHg, in order to maintain the above-described reaction temperature. Examples of quite suitable solvents are n-hexanol (b.p. 157° C.), cyclohexanol (b.p. 160° C.), 2-ethylhexanol (b.p. 184° C.), 3-methoxybutanol (b.p. 160° C.), furfuryl alcohol (b.p. 170° C.), and tetrahydrofurfuryl alcohol (b.p. 178° C.).

(3) A method which involves adjusting the mean residence time of the reaction mixture in the reaction zone, separately evaporating the effluent from the reactor to separate the hexamethyleneimine either alone or together with the solvent, and recycling the residue to the reaction zone. A preferred mean residence time of the reaction mixture in this case is about 90 minutes or less, e.g., about 15 minutes to about 90 minutes.

These methods can be used either individually or as a combination of two or more thereof.

In the present invention, the reaction pressure can be varied over a wide range. Usually, the pressure employed can range from about 30 mmHg to 8 Kg/cm$^2$ although the pressure will differ depending upon the above-described conditions and the type of the solvent chosen.

The process of this invention can be performed in the presence of some amount of hydrogen as in the case of ordinary hydrogenation reactions. A preferred partial pressure of hydrogen is about 5 Kg/cm$^2$ or less. Surprisingly, however, an important advantage in this invention is that the reaction can be performed in the absence of hydrogen. According to this invention, the reaction can be carried out at atmospheric or reduced pressure, e.g., about atmospheric pressure to about 30 mmHg, without any supply of hydrogen. In the prior art, the performance of a dehydrogenation reaction in the presence of hydrogen is intended primarily to prolong the active lifetime of the catalyst. According to the present invention, it is not particularly necessary to supply hydrogen to the reaction system because the catalyst is always washed with the inert solvent during the reaction and the ammonia and hexamethyleneimine formed during the reaction are always removed from the reaction system thereby to maintain the surface of the catalyst always in a fresh and highly active state. Usually, the use of hydrogen on an industrial scale involves the economic disadvantages of constructing hydrogen production facilities and the danger of explosion. The danger of explosion increases especially when air is likely to enter the reaction system. Further, in view of the fact that hydrogen gas is explosive over a wide range of conditions, the advantage that hydrogen is not required is important.

The process of this invention will be described in greater detail below.

Since the reaction in accordance with the present invention is performed while effectively removing the resulting hexamethyleneimine from the reaction system, ammonia formed during the reaction can be removed from the reaction system more easily than the hexamethyleneimine. In the present invention, however, no positive supply of ammonia is required, unlike the process described in Canadian Pat. No. 920,606. Rather, in the present invention ammonia is preferably positively removed from the reaction system.

Suitable techniques for removing the ammonia include (a) volatilization of the ammonia gas in advance of the distillation off of the azeotropic mixture during distillation; (b) volatilization of the ammonia gas in advance of the distillation of hexamethyleneimine or a mixture of hexamethyleneimine and the organic solvent during the distillation; (c) blowing hydrogen gas into the mixture to drive off the ammonia; and (d) removal of the ammonia gas under a vacuum.

In a preferred embodiment of this invention, a solvent which is insoluble in water but forms an azeotropic mixture with water and has higher compatibility with hexamethyleneimine than with water is selected as the inert organic solvent to be used. This enables the resulting hexamethyleneimine and by-product ammonia to be distilled out of the reaction system by an azeotropic distillation together with the solvent and water. The distillate is separated into two phases, and a greater part of the hexamethyleneimine is extracted into the solvent phase. Subsequently, the solvent can be recovered by means of a solvent recovering tower, and then recycled to the reaction system. Examples of the suitable solvents applicable to this embodiment are methylcyclohexne (azeotropic point: 81° C.), octane (azeotropic point: 89° C.), cumene (azeotropic point: 94° C.), mesitylene (azeotropic point: 96.5° C.), tert-amyl alcohol (azeotropic point: 87.4° C.), n-hexyl alcohol (azeotropic point: 98° C.), n-octyl alcohol (azeotropic point: 99.4° C.), benzyl alcohol (azeotropic point: 99.9° C.), cyclopentanol (azeotropic point: 96.3° C.), cyclohexanol (azeotropic point: 97.8° C.), di-n-butyl ether (azeotropic point: 93° C.), ethyl n-hexyl ether (azeotropic point: 92.5° C.), n-amyl ether (azeotropic point: 98.4° C.), and toluene (azeotropic point: 84° C.).

Another point which must be observed in performing the process of this invention is that the starting hexamethylenediamine should be purified as much as possible.

The following Examples are given to illustrate the present invention more specifically. Unless otherwise indicated, all parts, percents, ratios and the like are by weight.

EXAMPLE 1

In a 1-liter autoclave equipped with a stirrer, 200 g of Raney nickel catalyst was dispersed in 300 g of ethyl alcohol, and while maintaining the reaction pressure at 4.5 Kg/cm$^2$ with hydrogen and the reaction temperature at 115° C., a 30% ethyl alcohol solution of hexamethylenediamine was fed into the autoclave at each of the feed rates shown in Table 1 below. The reaction liquid was collected in a receiver as a clear solution via a stainless steel wire gauze filter fitted to the outlet of the reactor. By varying the rate of feeding the hexamethylenediamine solution, the mean residence time of the reaction liquid in the reactor was adjusted. Separately, these procedures were performed three times by varying the mean residence time. The reaction liquid in the receiver was analyzed, and the conversion of hexamethylenediamine and the selectivity of hexamethyleneimine were calculated. At the same time, the same analysis was made with regard to the reaction liquid in the reactor. The results obtained on varying the mean residence times at 60, 90, and 120 minutes are shown in Table 1 below.

TABLE 1

| Run No. | Rate of Feeding 30% HMD Solution (g/hr) | Mean Residence (hours) | Conversion of HMD (%) | Selectivity of HMI (%) | Concentration in Reactor HMD (%) | HMI (%) |
|---|---|---|---|---|---|---|
| 1 | 803 | 1.0 | 56 | 85 | 8.8 | 9.5 |
| 2 | 535 | 1.5 | 73 | 64 | 5.4 | 9.3 |
| 3 | 268 | 3.0 | 93 | 33 | 1.4 | 6.1 |

*HMD = hexamethylenediamine, HMI = hexamethyleneimine

EXAMPLE 2

30 g of Raney nickel catalyst immediately after preparation was washed twice with 100 g of tetrahydrofuran at 66° C. by a decantation method after removing water, and then washed five times with water. The catalyst so treated was then dispersed in 250 ml. of water with vigorous stirring. Purified hexamethylenediamine was added dropwise at a rate of 20 g per hour to the reaction system held at a temperature of 100° C., and hydrogen gas was introduced into the system at a space velocity of 35 ml. per minute. The reaction began immediately. The resulting hexamethyleneimine formed an azeotrope with water, and was collected through a rectifying column fitted to the reactor. At the same time, the by-product ammonia and the excess hydrogen gas were discharged from the tower as off-gases.

Hexamethylenediamine was added dropwise over the course of about 3 hours, and the reaction was continued for an additional 2 hours. The distillate and the residue in the reactor were analyzed by gas-chromatography, and it was found that the conversion of hexamethylenediamine was 100%, and the yield of hexamethyleneimine was 82%. During the reaction, the concentrations of hexamethylenediamine and hexamethyleneimine in the reaction mixture were both less than 5%. The amounts of by-products were 7%, bis-hexamethylenetetramine (BHT), 2% 6-hexamethyleneimino-1-aminohexane (HAH), and 9% (polyamine), respectively.

EXAMPLE 3

40 g of Raney nickel catalyst was dispersed in 250 ml. of water, and 1.6 g of sodium hydroxide was added to the resulting slurry. A 50% aqueous solution of hexamethylenediamine was fed into the resulting slurry at a rate of 80 g per hour. The reaction temperature was adjusted to 101° C., and hydrogen gas was introduced at a space velocity of 50 ml. per minute. The resulting hexamethyleneimine was collected by azeotropic distillation in the same way as in Example 1.

The reaction was continued for 33 hours, and then the reaction product was analyzed. It was found that the conversion of hexamethylenediamine was nearly 100%, the yield of hexamethyleneimine was 75%, and a polyamine was formed in a yield of 23%. Other by-products were formed only in trace amounts.

During the reaction, the concentrations of hexamethylenediamine and hexamethyleneimine in the reaction mixture were both less than 5%.

EXAMPLE 4

Hexamethyleneimine was prepared in the same way as in Example 2 using 30 g of Urushibara nickel prepared separately. The conversion of hexamethylenediamine was 85%, and the selectivity of hexamethyleneimine was 73%. The selectivities of BHT and HAH were 21% and 4%, respectively. The selectivity of polyamine was 2%. During the reaction, the concentrations of hexamethylenediamine and hexamethyleneimine in the reaction mixture were both less than 5%.

The Urushibara nickel was prepared by the method disclosed in Bull. Chem. Soc. Japan, Vol. 27, page 480 (1954).

EXAMPLE 5

Using 30 g of a powder of nickel metal prepared by heat-decomposing nickel formate at 270° C., hexamethyleneimine was prepared in the same way as in Example 2. The conversion of hexamethylenediamine was 53%, and the selectivity was 79% for hexamethyleneimine, 14% for BHT, and 7% for HAH. No polyamine was formed. During the reaction, the concentrations of hexamethylenediamine and hexamethyleneimine in the reaction mixture were less than 15%, and less than 5%, respectively.

EXAMPLE 6

Hexamethyleneimine was prepared in the same way as in Example 2 using 60 g of a powdery nickel catalyst (nickel content 50%; the size being such that it passed through a 150-mesh sieve) supported on kieselgur. As a result, the conversion of hexamethylenediamine was 39%, and the percentages of the products based on the converted hexamethylenediamine were 71% for hexamethyleneimine, 24% for BHT, 3% for HAH, and 2% for 1,6-dihexamethyleneiminohexane. No polyamine was formed.

During the reaction, the concentrations of hexamethylenediamine and hexamethyleneimine in the reaction mixture were less than 20%, and less than 5%, respectively.

EXAMPLE 7

A 3-liter autoclave equipped with a stirrer, a fractional distilling tower at the top of the tower equipped with a reflux condenser and a withdrawal device, and a hydrogen-introducing tube was charged with 300 g of Raney nickel and 900 ml. of water. These materials were heated with vigorous stirring, and the reaction system was pressurized with hydrogen. Thus, the reaction system was maintained at a temperature of 150° C. and a pressure of 6 atmospheres. A 50% aqueous solution of purified hexamethylenediamine was fed into the autoclave at a rate of 200 ml. per hour, and simultaneously, hydrogen gas was introduced at a space velocity of 35 ml. per minute. The resulting hexamethyleneimine-water azeotropic mixture was collected at a receiver through the fractional distilling column and the reflux condenser, and the rate of distillation was adjusted correspondingly to the rate of feeding the starting material. The 50% aqueous solution of hexamethylaminediamine was fed over the course of 10 hours, and the reaction was continued for an additional 2 hours. The distillate and the residue in the reactor were analyzed by gas-chromatography. It was found that the conversion of hexamethylenediamine was 100%, and the yield of hexamethyleneimine was 81%. The yields of the by-products BHT and HAH were 9%, and 1.5%, respectively. The yield of polyamine was 6%.

During the reaction, the concentrations of hexamethylenediamine and hexamethyleneimine in the reaction mixture were both less than 5%.

EXAMPLE 8

60 g of Raney cobalt catalyst was dispersed in 250 ml. of water to form a slurry of the catalyst. 58 g of purified hexamethylenediamine was added dropwise at a rate of 20 g per hour to the reaction system held at 100° C., and hydrogen gas was introduced at a space velocity of 50 ml. per minute. The reaction began immediately. The resulting hexamethyleneimine was collected as an azeotrope with water through a rectifying column fitted to the reactor, and simultaneously, the by-product ammonia gas and the excess hydrogen gas were recovered as off-gases from the top of the column.

Hexamethylenediamine was added dropwise over the course of about 3 hours, and the reaction was continued for an additional 3 hours. The distillate and the residue in the reactor were analyzed by gas-chromatography. It was found that the conversion of hexamethylenediamine was 53%, and the selectivity of hexamethyleneimine was 88%. The remaining 12% of the reaction product was all BHT, and no polyamine or other by-products were formed at all.

During the reaction, the concentrations of hexamethylenediamine and hexamethyleneimine in the reaction mixture were both less than 5%.

EXAMPLE 9

A 3-liter autoclave equipped with a stirrer, a hydrogen-inlet tube and a reflux condenser with a distillate withdrawing device at the top of the condenser was charged with 300 g of reduced cobalt and 900 ml. of water. With vigorous stirring the catalyst slurry was heated, and the inside of the autoclave was pressurized with hydrogen. Thus, the reaction system was maintained at a temperature of 150° C. and a pressure of 6 atmospheres. A 50% aqueous solution of purified hexamethylenediamine was fed into the autoclave at a rate of 200 ml. per hour, and simultaneously, hydrogen gas was introduced at a space velocity of 35 ml. per minute. The resulting hexamethyleneimine/water azeotrope was collected at a receiver through the fractional distilling tower and the reflux condenser. The rate of distillation was adjusted to correspond to the rate of feeding the starting material. The 50% aqueous solution of hexamethylenediamine was fed over the course of 10 hours, and then, the mixture was heated with stirring for an additonal 2 hours. The distillate and the residue in the reactor were analyzed by gas-chromatography. It was found that the conversion of hexamethylenediamine was 58%, and the selectivity of hexamethyleneimine was 82%. In addition, 9% of BHT and a liquid material were formed.

During the reaction, the concentrations of hexamethylenediamine and hexamethyleneimine in the reaction mixture were both less than 5%.

EXAMPLE 10

In a 300 ml. reaction flask, 10 g of Raney nickel catalyst was dispersed in 100 ml. of each of the various solvents shown in Table 2 below with stirring. While the temperature of the dispersion was maintained at each of the points shown in Table 2, 58 g of purified hexamethylenediamine was added dropwise at a rate of 20 g per hour, and hydrogen gas was introduced at a space velocity of 30 ml. per minute. The reaction began immediately. The resulting hexamethyleneimine was removed from the reaction system using each of the methods shown in Table 2 successively and rapidly. During the reaction, the concentrations of hexamethylenediamine and hexamethyleneimine in the reaction mixture were both less than 5%.

Simultaneously with the completion of the addition of hexamethylenediamine, the reaction was stopped. The unreacted hexamethylenediamine in the reaction mixture, and hexamethyleneimine removed from the reaction system were quantitatively determined by gas-chromatography, and the conversion of hexamethyleneidiamine and the selectivity of hexamethyleneimine were measured. The results obtained are shown in Table 2.

TABLE 2

| Run No. | Solvent Type | Boiling Point (°C.) | Reaction Temperature (°C.) | Method of Removing Hexamethyleneimine | Conversion of HMD (%) | Selectivity of HMI (%) |
|---|---|---|---|---|---|---|
| 1 | Furfuryl Alcohol | 170 | 120 | Distillation at reduced pressure (100 mmHg) | 89 | 84 |
| 2 | Cyclohexanol | 161 | 110 | Distillation at 250 mmHg | 94 | 92 |
| 3 | Octanol | 195 | 150 | Distillation | 92 | 79 |
| 4 | Ethylene Glycol | 198 | 100 | Azeotroping with water using | 75 | 74 |
| 5 | Tetralin | 207 | 100 | Distillation at reduced pressure | 83 | 82 |
| 6 | Decalin | 190 | 160 | Distillation | 96 | 77 |
| 7 | Tetrahydrofurfuryl Alcohol | 178 | 120 | Distillation at 80 mmHg | 95 | 85 |
| 8 | Anisole | 154 | 145 | Distillation | 98 | 80 |
| 9 | Phenyl Propyl Ether | 190 | 140 | Distillation | 99 | 83 |
| 10 | Di-n-Amyl Ether | 190 | 150 | Distillation | 99 | 75 |
| 11 | Xylene (Comparison) | 138 | 138 | HMI vapor was condensed by refluxing and recycled to the reaction system (not removed) | 93 | 7 |

As shown by the results in Table 2, by performing the reaction while removing the resulting hexamethyleneimine immediately from the reaction system, high selectivities of hexamethyleneimine could be achieved. On the other hand, the selectivity was very low in the comparison run (Run No. 11) in which the reaction was performed while leaving the resulting hexamethyleneimine in the reaction mixture. Accordingly, the effect of the present invention is very marked.

EXAMPLE 11

In an autoclave equipped with an electromagnetically driven stirrer and a hexamethyleneimine-discharging device at the upper part of the autoclave, 20 g of Raney cobalt catalyst was dispersed in 100 ml. of each of the solvents shown in Table 3 below. While maintaining the reaction temperature at 132° C. and also passing hydrogen gas to control the reaction pressure at 3 Kg/cm$^2$, 387 g of a 30% aqueous solution of purified hexamethylenediamine was fed into the autoclave over the course of 3 hours using a pump.

The reaction began immediately, and the generated ammonia was discharged from the reaction system while replacing the ammonia with hydrogen. The resulting hexamethyleneimine was collected as an azeotrope with water by azeotropic distillation at this pressure.

During the reaction, the concentrations of hexamethylenediamine and hexamethyleneimine in the reaction mixture were less than 15%, and less than 5%, respectively.

Upon completion of the feeding of the hexamethylenediamine, the reaction was stopped. The unreacted hexamethylenediamine in the reaction mixture and the hexamethyleneimine in the distillate were both quantitatively determined by gas-chromatography, and the conversion of hexamethylenediamine and the selectivity of hexamethyleneimine were measured. The results obtained are shown in Table 3.

TABLE 3

| Run No. | Solvent | Conversion of HMD (%) | Selectivity of HMI (%) |
|---|---|---|---|
| 1 | n-Amyl Alcohol | 86 | 89 |
| 2 | n-Octane | 79 | 82 |
| 3 | Cumene | 75 | 78 |
| 4 | Di-n-butyl Ether | 82 | 85 |
| 5 (Comparison) | Di-n-butyl Ether | 71 | 23 |

The results in Table 3 demonstrate that in Run Nos. 1 to 4 in accordance with this invention, the conversion of hexamethylenediamine and the selectivity of hexamethyleneimine were very high.

Run No. 5 (comparison) was performed under the same conditions as in Runs 1 to 4 above except that the resulting hexamethyleneimine and ammonia were not removed from the reaction system. The selectivity of hexamethyleneimine was very low.

EXAMPLE 12

In a 1-liter reactor equipped with a stirrer, 30 g of Raney nickel catalyst was dispersed in 200 ml. of cyclohexanol with good stirring. While maintaining the temperature at 105° C., 116 g of purified hexamethylenediamine was added dropwise over the course of 2 hours, and simultaneously, hydrogen gas was introduced thereinto at a space velocity of 35 ml. per minute. The reaction begin immediately, and upon the generation of ammonia, hexamethyleneimine also began to be formed.

The resulting hexamethyleneimine was separated from the solvent by distillation while allowing the reaction mixture to stand at reduced pressure. The concentration of hexamethyleneimine in the reaction mixture was changed as shown in Table 4 below by changing the degree of pressure reduction, and the selectivity of hexamethyleneimine was measured. The concentration of hexamethylenediamine in the reaction mixture was less than 5%. The results obtained are shown in Table 4.

TABLE 4

| Run No. | Concentration of HMI Remaining in Reaction Mixture (%) | Conversion of HMD (%) | selectivity of HMI (%) |
|---|---|---|---|
| 1 | 1.1 | 99 | 89 |
| 2 | 1.8 | 99 | 88 |
| 3 | 4.6 | 98 | 84 |
| 4 | 9.3 | 99 | 69 |
| 5 (comparison) | 14.2 | 97 | 57 |

The results shown in Table 4 demonstrate that the selectivity of hexamethyleneimine decreases abruptly with increasing concentration of hexamethylenediamine in the reaction mixture.

EXAMPLE 13

A 200 ml. reaction flask was charged with 110 g of cumene and 10 g of Raney nickel catalyst, and with stirring, a dispersion of the catalyst in cumene was prepared. While maintaining the temperature at 97° C., 194 g of a 30% aqueous solution of purified hexamethylenediamine was added dropwise to the dispersion over the course of 3 hours, and simultaneously, hydrogen gas was introduced at a space velocity of 65 ml. per minute.

The reaction began immediately, and upon the generation of ammonia, the resulting hexamethyleneimine formed an azeotrope with water which was condensed through a condenser after leaving a distillation tower fitted to the flask. During the reaction, the concentrations of hexamethylenediamine and hexamethyleneimine in the reaction mixture were both less than 5%.

As a result of the distillation, 34.0 g of hexamethyleneimine, 83.3 g of cumene, 78.8 g of water and 7.3 g of ammonia were distilled out. Ammonia was discharged as a non-condensed gas together with the hydrogen gas, while only a part of the ammonia dissolved in water.

The condensed liquid separated into two phases, a light phase containing 28.6 g of hexamethyleneimine and 83.3 g of cumene, and a heavy phase containing 5.4 g of hexamethyleneimine and 78.8 g of water. The heavy phase was further distilled to recover 5.4 g of hexamethylenediamine and 5.4 g of water as an azeotrope. The recovered hexamethyleneimine was mixed with the light phase, and extracted to afford 35.6 g of hexamethyleneimine and 83.3 g of cumene. The aqueous phase contained 5.4 g of water and 0.4 g of hexamethyleneimine.

The extract was distilled to separate and recover hexamethyleneimine from the tower top and cumene from the bottom.

A tiny amount of hexamethyleneimine remaining in the aqueous phase could be recovered completely by mixing the aqueous phase with the heavy phase and distilling the mixture repeatedly.

The residual liquid in the reaction flask was analyzed by gas-chromatography to determine quantitatively the unreacted hexamethylenediamine and the by-product BHT and HAH. It was found that the conversion of hexamethylenediamine was 86%, and the selectivitly was 80% for hexamethyleneimine, 8% for BHT and 12% for HAH. Only trace amounts of polyamine and tar were formed.

EXAMPLE 14

A 2-liter flask was charged with 450 g of 3-methoxybutanol and 60 g of Raney nickel, and with vigorous stirring, the temperature was maintained at 105° C. A 25% 3-methoxybutanol solution of hexamethylenediamine was added dropwise in an amount of 500 g over the course of 3 hours. The reaction pressure was adjusted to 180 mmHg using a vacuum pump, and hydrogen was not affirmatively supplied at all to the reaction system.

As soon as the hexamethylenediamine solution began to be added dropwise, the reaction was initiated. The resulting hexamethyleneimine evaporated off together with the 3-methoxybutanol solvent. It was liquefied by a condenser, and then collected. The by-product ammonia gas was removed using a vacuum pump.

After adding all of the hexamethylenediamine solution, the reaction was performed for an additional 30 minutes. Then the reaction was stopped to afford 275 g of an evaporated liquid. During the reaction, the concentration of hexamethylenediamine and hexamethyleneimine in the reaction mixture were both less than 5%. The conversion of hexamethylenediamine was more than 99%.

Gas-chromatographic analysis showed that the evaporated liquid contained 83 g of hexamethyleneimine. Further, 9 g of hexamethyleneimine, 8 g of BHT and 5 g of HAH remained in the reactor. The yield of hexamethyleneimine was found to be 86%.

EXAMPLE 15

A 500 ml. flask was charged with 200 g of a 90:10 mixture of cumene and cyclohexanol, 50 g of hexamethylenediamine and 30 g of Raney nickel. With vigorous stirring, the temperature was maintained at 100° C., and the reaction of hexamethylenediamine was initiated. The reaction pressure was adjusted to 200 mmHg using a vacuum pump, and hydrogen was not affirmatively supplied to the reaction system. While removing the resulting hexamethyleneimine and the by-product ammonia from the reaction system, the reaction was performed for 1.5 hours to afford 93 g of a distillate. During the reaction, the concentrations of hexamethylenediamine and hexamethyleneimine in the reaction mixture were both less than 5%.

The conversion of hexamethylenediamine was found to be nearly 100%. Gas-chromatographic analysis showed that the distillate contained 32 g of hexamethyleneimine, and in the reactor, 3 g of hexamethyleneimine, 5 g of BHT and 3 g of HAH remained. The yield of hexamethyleneimine was 82%.

EXAMPLE 16

A 30-liter reactor equipped with a stirrer was charged with 7.5 Kg of 2-ethylhexanol and 2.5 Kg of Raney nickel, and a 10% 2-ethylhexanol solution of hexamethylenediamine was fed into the reactor at a rate of 1.46 Kg (as hexamethylenediamine) per hour. During the reaction, the temperature was maintained at 110° C., and the pressure, at 40 mmHg. Hydrogen was not supplied affirmatively. During the reaction, the concentrations of hexamethylenediamine and hexamethyleneimine in the reaction mixture were both less than 5%.

The resulting hexamethyleneimine was liquefied through a condenser from a gas line equipped at the top of the reactor, and collected. The by-product ammonia was removed using a vacuum device.

The by-product BHT, HAH and polyamine were removed by flowing them from an overflow line of the reactor. At this time, the Raney nickel accompanied the overflow at a rate of of 30 g per hour. Fresh Raney nickel was supplied to make up for this loss.

After continuing the reaction for 48 hours, the average rate of hexamethyleneimine formed was 1.0 Kg/hour. The yield of the hexamethyleneimine was 80%.

EXAMPLE 17

In a 300 ml. reaction flask, 150 ml. of n-hexanol was added, and 20 g of Raney catalyst was dispersed in the n-hexanol with stirring. While maintaining the temperature at 100° C., 60 g of purified hexamethylenediamine was added dropwise at a rate of 20 g per hour, and simultaneously, steam was introduced into the system. Hydrogen was not affirmatively supplied.

The reaction began immediately. The resulting hexamethyleneimine was distilled out of the reaction system together with water and n-hexanol. The resulting ammonia was discharged at the same time. During the reaction, the concentrations of hexamethylenediamine and hexamethyleneimine in the reaction mixture were both less than 5%.

Upon adding all of the hexamethylenediamine, the reaction was stopped. A tiny amount of hexamethyleneimine remained in the reaction mixture and the unreacted hexamethylenediamine and the distilled hexamethyleneimine were quantitatively determined by gas-chromatography.

The conversion of hexamethylenediamine was 94%, and the yield of hexamethyleneimine was 78%. The selectivity of the hexamethyleneimine was 84%.

While the invention has been described in detail and with reference to specific embodiments thereof, it will be apparent to one skilled in the art that various changes and modifications can be made therein without departing from the spirit and scope thereof.

What is claimed is:

1. A process for preparing hexamethyleneimine from hexamethylenediamine, which comprises the steps of continuously reacting hexamethylenediamine in the absence of hydrogen at about 80° to 150° C., 30 mmHg to 8 kg/cm$^2$ pressure in an inert solvent using a nickel catalyst and/or cobalt catalyst while maintaining the concentrations of hexamethyleneimine and hexamethylenediamine in the reaction mixture at 5% by weight or less and 10% by weight or less, respectively, by removing the hexamethyleneimine from the reaction system as soon as the hexamethyleneimine is formed.

2. The process of claim 1, wherein said inert solvent is water.

3. The process of claim 1, wherein said inert solvent is an inert organic solvent.

4. The process of claim 1, wherein said inert solvent is cyclohexanol, n-hexanol, 3-methoxybutyl alcohol, 2-ethyl hexanol, furfuryl alcohol, or tetrahydrofurfuryl alcohol.

5. The process of claim 2, wherein the removing of the hexamethyleneimine from the reaction system is by distilling the hexamethyleneimine off as an azeotrope with water.

6. The process of claim 1, wherein the removing of the hexamethyleneimine from the reaction system is at reduced pressure.

7. The process of claim 1, wherein said inert solvent is a solvent which is insoluble in water and forms an azeotrope with water and has a higher compatibility with hexamethyleneimine than with water, and wherein the process includes distilling off hexamethyleneimine, water and the solvent during the reaction, cooling and separating the distillate into two phases, and extracting a greater part of the hexamethyleneimine into the solvent phase.

8. The process of claim 1, wherein said inert solvent has a boiling point of 100° to 250° C.

9. The process of claim 1, wherein the mean residence time of the reaction mixture in the reaction zone is about 90 minutes or less.

10. The process of claim 1 wherein said inert solvent is an alcohol.

11. The process of claim 10 wherein said inert solvent is an alcohol selected from the group consisting of aliphatic alcohols, alicyclic alcohols and benzene ring-substituted aliphatic alcohols.

12. The process of claim 1 wherein said reaction is carried out at a temperature of about 95° to 150° C.

* * * * *